United States Patent [19]

Yamada

[11] Patent Number: 5,756,488
[45] Date of Patent: May 26, 1998

[54] COMPOSITION FOR IMPROVING CALCIUM METABOLISM

[75] Inventor: Sachiko Yamada, 1227-4, Hatsuzawa-cho, Hachioji-shi, Tokyo, Japan

[73] Assignees: Kuraray Co., Ltd., Kurashiki; Sachiko Yamada, Hachioji, both of Japan

[21] Appl. No.: 655,973

[22] Filed: May 31, 1996

[30] Foreign Application Priority Data

Jul. 31, 1995 [JP] Japan ................................ 7-215175
Oct. 25, 1995 [JP] Japan ................................ 7-302167

[51] Int. Cl.$^6$ .................................................... A61K 31/59
[52] U.S. Cl. ................................................................ 514/167
[58] Field of Search ........................................ 514/167

[56] References Cited

U.S. PATENT DOCUMENTS 4,929,610   5/1990   Meier et al. ........................ 514/167

FOREIGN PATENT DOCUMENTS 6-25155   2/1994   Japan .

OTHER PUBLICATIONS

J. Nutr. Sci. Vitaminol., vol. 35, pp. 529–533, 1989, Toshio Okano, et al., "Protein–Binding Properties of 22–Oxa–1α, 25–Dihydroxyvitamin $D_3$, A Synthetic Analogue of 1α,25–Dihydroxyvitamin $D_3$".

J. Biochem., vol. 115, pp. 373–380, 1994, Tadashi Kobayashi, et al., "The Binding Properties, With Blood Proteins, and Tissue Distribution of 22–Oxa–1α,25–Dihydroxyvitamin $D_3$, A Noncalcemic Analogue of 1α,25–Dihydroxyvitamin $D_3$, in Rats".

Endocrine Reviews, vol. 16, No. 2, pp. 200–257, 1995, Roger Bouillon, et al., "Structure–Function Relationships in the Vitamin D Endocrine System".

*Primary Examiner*—Theodore J. Criares
*Attorney, Agent, or Firm*—Oblon, Spivak, McClelland, Maier & Neustadt, P.C.

[57] ABSTRACT

A composition for improving calcium metabolism comprising, as an active ingredient, (20S,22R)-22-methyl-1α,25-dihydroxyvitamin $D_3$; and a method of treating a calcium metabolism disorder in a mammal comprising administering a therapeutically effective amount of (20S, 22R)-22-methyl-1α,25-dihydroxyvitamin $D_3$.

3 Claims, No Drawings

COMPOSITION FOR IMPROVING CALCIUM METABOLISM

BACKGROUND OF THE INVENTION

1. Field of the Invention

The present invention relates to a pharmaceutical composition for improving calcium metabolism comprising (20S, 22R)-22-methyl-1α,25-dihydroxyvitamin $D_3$ as an active ingredient, and to a method of treating calcium metabolism disorders using the pharmaceutical composition.

2. Discussion of the Related Art

With the progress of research of vitamin D in recent years, various 1α-hydroxyvitamin D derivatives have been developed for medical purposes. For example, 22-oxa-1,25-dihydroxyvitamin $D_3$ which binds to the 1,25-dihydroxyvitamin $D_3$ receptor (hereinafter simply referred to as the $D_3$ receptor) in one-eighth the affinity of 1,25-dihydroxyvitamin $D_3$ and binds to vitamin D-binding protein in as low affinity as about one six-hundredth the affinity of 1,25-dihydroxyvitamin $D_3$, has been under investigation as a therapeutic agent for hyperparathyroidism (J. Nutr. Sci. Vitaminol., 35, .529 (1989), J. Biochemistry, 115, 373(1994)).

Also it is known that a vitamin D derivative having a methyl group at the 22-position has the same degree of affinity for the $D_3$ receptor as that of 1,25-dihydroxyvitamin $D_3$ (Japanese Patent Laid-Open No.6-25155).

However, development of vitamin D derivatives, which have a higher affinity for the $D_3$ receptor and higher safety than the above existing compounds, have been in need.

SUMMARY OF THE INVENTION

Accordingly, an object of the present invention is to provide a composition for improving calcium metabolism comprising, as an active ingredient, a vitamin $D_3$ derivative with a high affinity for the $D_3$ receptor and high safety for therapeutic uses.

Another object of the invention is to provide a method of treating calcium metabolism disorders using the composition.

In order to achieve the above objects, the present inventor intensively studied various vitamin $D_3$ derivatives. As a result, it was found that among 4 isomers of 22-methyl-1α, 25-dihydroxyvitamin $D_3$, which differ in the configuration at the 20- and 22-positions, (20S,22R)-22-methyl-1α,25-dihydroxyvitamin $D_3$ showed a significantly higher affinity for the $D_3$ receptor and a lower affinity for vitamin D-binding protein as compared with other isomers.

Specifically, it has been found that (20S,22S)-22-methyl-1α,25-dihydroxyvitamin $D_3$ binds to the $D_3$ receptor in one four-hundredth the affinity of 1α,25-dihydroxyvitamin $D_3$, whereas, unexpectedly, (20S,22R)-22 -methyl-1α,25-dihydroxyvitamin $D_3$, the derivative of the present invention, has an affinity 18 times as high as that of 1α, 25-dihydroxyvitamin $D_3$. Of known vitamin $D_3$ derivatives, there are only a few derivatives which have a higher affinity for the $D_3$ receptor than that of natural 1α,25-dihydroxyvitamin $D_3$, and, at best, their affinity for the $D_3$ receptor is only 2 to 3 times higher than that of natural 1α,25-dihydroxyvitamin $D_3$ [Endocrine Reviews, 16(2), 200(1995)]. Therefore, it is a surprising discovery that the derivative of the present invention has an affinity 18 times as high as that of natural 1α,25-dihydroxyvitamin $D_3$.

Based upon the above findings, the present invention has been completed.

The gist of the present invention is as follows:

(1) A composition for improving calcium metabolism comprising, as an active ingredient, (20S,22R)-22-methyl-1α,25-dihydroxyvitamin $D_3$ represented by the following formula (I):

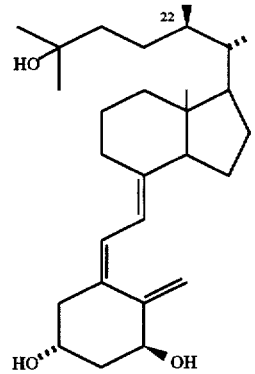

and (2) A method of treating a calcium metabolism disorder in a mammal comprising administering to the mammal a therapeutically effective amount of (20S,22R)-22-methyl-1α,25-dihydroxyvitamin $D_3$ represented by the following formula (I):

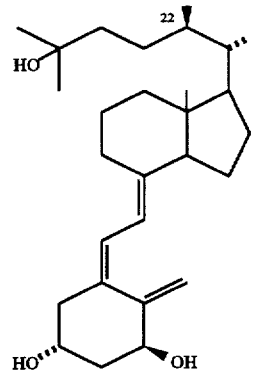

According to the present invention, a pharmaceutical composition for improving calcium metabolism comprising (20S,22R)-22-methyl-1α,25-dihydroxyvitamin $D_3$, which has a high affinity for the $D_3$ receptor and high safety for therapeutic purposes, can be provided. The present invention can also provide a method of treating calcium metabolism disorders in a mammal in which a therapeutically effective dose of (20S,22R)-22-methyl-1α,25-dihydroxyvitamin $D_3$ is given to the mammal.

DETAILED DESCRIPTION OF THE INVENTION

The present invention is described in more detail below.

(20S,22R)-22-methyl-1α,25-dihydroxyvitamin $D_3$ represented by formula (I) can be produced by a conventional method using (20S,22R)-22-methylprovitamin D derivatives. Specifically, it can be produced by photoisomerizing, for example, (20S,22R)-22-methylprovitamin D derivatives under an oxygen-free condition, and further thermally isomerizing the resulting isomers. The details of the method for producing (20S,22R)-22-methyl-1α,25-dihydroxyvitamin $D_3$, including the synthesis of the provitamin D, are described in Japanese Patent Laid-Open No. 6-25155.

(20S,22R)-22-methyl-1α,25-dihydroxyvitamin $D_3$ thus obtained can be isolated and purified according to a conventional method which is used for isolating and purifying an organic compound in a reaction mixture. For example, a crude product is first obtained by concentrating a reaction mixture, which is then purified by chromatographies.

As evident from the results of the Experimental Examples mentioned below, (20S,22R)-22-methyl-1α,25-dihydroxyvitamin $D_3$ represented by formula (I) has a much higher affinity for the $D_3$ receptor than 1,25-dihydroxyvitamin $D_3$, namely its affinity is 18 times higher than that of 1,25-dihydroxyvitamin $D_3$, whereas the affinity of (20S,22R)-22-methyl-1α,25-dihydroxyvitamin $D_3$ for vitamin D-binding protein is as low as one five-hundredth the affinity of 1,25-dihydroxyvitamin $D_3$. Also, this compound was found to have low toxicity in acute toxicity tests. These findings supports the usefulness of this compound as a safe agent for improving calcium metabolism, for example, in the therapy of hyperparathyroidism.

A pharmaceutical composition for improving calcium metabolism containing (20S,22R)-22-methyl-1α,25-dihydroxyvitamin D3 represented by formula (I) as an active ingredient can be administered via oral or parenteral route in an appropriate dosage form. The dose depends on patient's age, symptom, route of administration, etc. For example, when it is indicated for prevention or treatment of calcium metabolism disorders in adults, usually 0.01–5 μg, preferably 0.05–1 μg is administered t.i.d. It is of course possible to exceed the above range at the discretion of the doctors.

The pharmaceutical composition for improving calcium metabolism of the present invention may contain pharmacologically acceptable vehicle or excipient as well as a therapeutically effective dose of the active ingredient. This composition can take dosage forms suitable for oral or parenteral administration.

Specifically, the dosage forms suitably used for oral administration include solid or liquid dosage forms, such as tablets, pills, granules, powder, capsules, syrup, emulsion, and suspension. These preparations can be produced by methods known in the art using vehicles or excipients commonly used in the pharmaceutical field. For example, vehicles and excipients for tablets include lactose, starch, sucrose, and magnesium stearate.

With respect to preparations for parenteral administration, injections, for example, may be prepared by conventional methods in the art. That is, the composition of the present invention is dissolved, suspended, or emulsified in a sterile aqueous or oil liquid for injection. Examples of aqueous liquids for injection include physiological saline and isotonic solution containing glucose and other supplemental ingredients, which may further contain a suitable solubilizing agent.

The pharmaceutical composition for improving calcium metabolism of the present invention may further contain other active ingredients as long as they do not cause undesirable interaction with (20S,22R)-22-methyl-1α,25-dihydroxyvitamin $D_3$.

EXAMPLES

The present invention is hereinafter described in more details by means of the following examples and experimental examples, but not limited by them in any ways.

Example 1

Synthesis of (20S 22R)-22-methyl-1α,25-dihydroxyvitamin $D_3$ 6.75 mg (0.0157 mmol) of (20S,22R)-22-methylcholesta-5,7-diene-1α,3β,25-triol, which was synthesized according to the method described in Japanese Patent Laid-Open No. 6-25155, was dissolved in 170 mL of benzene/ethanol (150:20) solution, into which highly pure argon gas (99.999%) was blown for 20 minutes. Then, the mixture was irradiated at 0° C. for 2 minutes with ultraviolet ray through a Vycor filter using 100 W high-pressure mercury lamp which had been stabilized for 5 minutes in advance. The reaction mixture thus obtained was concentrated and then subjected to chromatography with Sephadex® LH-20 column (Pharmacia) using a mixture of chloroform/hexane/methanol (70:30:0.7) as the eluting solvent to isolate the previtamin.

The previtamin thus obtained was dissolved in 5 ml of 95% ethanol, and allowed to stand for 2 weeks under argon atmosphere in dark place at room temperature. The reaction mixture was concentrated and then subjected to chromatography with Sephadex® LH-20 column using a mixture of chloroform/hexane/methanol (70:30:1) as the eluting solvent to isolate (20S,22R)-22-methyl-1α,25-dihydroxyvitamin $D_3$ (Compound 1). As a result, 1.68 mg (yield: 24.8%) of (20S,22R)-22-methyl-1α,25-dihydroxyvitamin $D_3$, which had the following physical properties, was obtained:

$^1$H-NMR spectrum, δ(ppm):

0.53 (3H, s, H-18), 0.75 and 0.86(each 3H, d, J=7.0 Hz, H-21 and H-22Me), 1.22 (6H, s, H-26 and H-27), 4.23 (1H, m, H-3), 4.43(1H, m, H-1), 5.00 and 5.33 (each 1H, s, H-19), 6.02 and 6.38 (each 1H, d, J=11.3Hz, H-7 and H-6)

Mass spectrum (EI) m/z (relative intensity):

412 ($M^+$ —$H_2O$, 18), 394 (82), 379(100), 251(35), 249 (23), 209(22), 197(22), 155(36), 141(21), 105(26), 69(22), 55(16)

Comparative Example 1

The same procedures as in Example 1 were carried out except that the configuration of the starting materials were different and the following compounds were synthesized: (20S,22S)-22-methyl-1α,25-dihydroxyvitamin $D_3$ (Compound 2), (20R,22R)-22-methyl-1α,25-dihydroxyvitamin $D_3$ (Compound 3), and (20R,22S)-22-methyl-1α,25-dihydroxyvitamin $D_3$ (Compound 4).

Experimental Example 1

Assay of Affinity for 1α,25-dihydroxyvitamin $D_3$ Receptor of Pig Small Intestine With Compounds 1 to 4 obtained in Example 1 and Comparative Example 1, the affinity of each test compound for 1α,25-dihydroxyvitamin $D_3$ receptor of pig small intestine was evaluated.

A solution of pig small intestinal nuclear extract was prepared according to the method of Dame [Proc. Natl. Acad. Sci. USA, 82, p7825 (1985)], which was diluted 1:30. To a test tube, 100 μl of the solution of pig small intestinal nuclear extract and 5p1 of ethanol solution of tritium-labeled 1α,25-dihydroxyvitamin $D_3$ (to make a final concentration of $10^{-9}$M) were added and stirred.

Separately, each of Compounds 1 to 4 was diluted stepwise with ethanol to make a series of ethanol solutions of each test compound with varying concentrations: 0.025, 0.05, 0.1, 0.25, 0.5, 1, 2.5, 10, 50, 250 and 1000 nM. To the above solution, each ethanol solution of the test compounds or only ethanol (as a blank) was added, and the mixture was stirred and allowed to stand in a shaking bath (shaking frequency:120 rpm) for 2 hours at room temperature. Next, to each of the reaction mixtures, 50 μl of hydroxyapatite suspension [Proc. Natl. Acad. Sci. USA, 82, p7825 (1985)] was added at 0° C., which was subjected to 10-minute stirring three times and then to centrifugation (600×g, 10 minutes) to remove the supernatant. The pellet thus obtained was washed with 0.5% Triton X-100/TED buffer solution [Proc.

Natl. Acad. Sci. USA, 82, p7825 (1985)] three times, and transferred to a scintillation vial containing Biosafe scintillator to determine the radioactivity. The percentage of tritium-labeled $1\alpha,25$-dihydroxyvitamin $D_3$ bound to the $D_3$ receptors was measured to determine the concentration of each test compound at which 50% of the tritium-labeled $1\alpha,25$-dihydroxyvitamin $D_3$ bound to the $D_3$ receptors was replaced with the test compound ($ED5_0$). As for Compound 1, a 60% replacement value was obtained because this compound showed a high affinity. As a control, the same procedures were followed using $1\alpha,25$-dihydroxyvitamin $D_3$, and $ED_{50}$ of this control was obtained. Using the $ED_{50}$ of the control as the reference, i.e., 1, the affinity of each test compound was calculated as shown in Table 1.

TABLE 1

| Test Compounds | Affinity |
| --- | --- |
| 1,25-dihydroxyvitamin $D_3$ (control) | 1 |
| Compound 1 | 18 |
| Compound 2 | 1/400 |
| Compound 3 | 1/60 |
| Compound 4 | 1/3 |

As shown in Table 1, it was found that Compound 1 had 18 times higher affinity for the $D_3$ receptor than that of $1\alpha,25$-dihydroxyvitamin $D_3$, the control.

Experimental Example 2
Assay of Affinity for $1\alpha,25$-dihydroxyvitamin $D_3$ Receptor of Bovine Thymus With Compounds 1 to 4 obtained in Example 1 and Comparative Example 1, the affinity of each test compound for $1\alpha,25$-dihydroxyvitamin $D_3$ receptor of bovine thymus was evaluated.

Specifically, each of Compounds 1 to 4 was diluted stepwise with ethanol to make a series of ethanol solutions of varying concentrations for each test compound: 8, 16, 32, 63, 125, 250, 500, and 5000 pg/50 μl of ethanol. To each of the solutions, a solution of tritium-labeled $1\alpha,25$-dihydroxyvitamin $D_3$ (about 5000 cpm) was added, to which bovine thymus $1\alpha,25$-dihydroxyvitamin $D_3$ receptor (produced by Yamasa K.K.) was added in an amount of 0.125 mg/500p1 phosphate buffer and stirred. After the mixture was allowed to stand overnight at 4° C., suspension of dextran-coated charcoal (DCC, produced by Yamasa K.K.) was added and stirred to adsorb the free test compound remaining unbound to the $D_3$ receptors. The reaction mixture was centrifuged at 3000 rpm to separate DCC, thereby separating the test compound bound with the $D_3$ receptors from the free test compound. With 500 μl of the supernatant, the radioactivity was measured by a scintillation counter. The percentage of tritium-labeled $1\alpha,25$-dihydroxyvitamin $D_3$ bound to the $D_3$ receptors was measured to determine the concentration of each test compound at which 50% of the tritium-labeled $1\alpha,25$-dihydroxyvitamin $D_3$ bound to the $D_3$ receptors was replaced with the test compound ($ED_{50}$). As for Compound 1, a 60% replacement value was determined because this compound showed a high affinity. As a control, the same procedures were followed using $1\alpha,25$-dihydroxyvitamin $D_3$, and $ED_{50}$ of this control was obtained. Using the $ED_{50}$ of the control as the reference, i.e., 1, the biding affinity of each test compound was calculated as shown in Table 2.

TABLE 2

| Test Compounds | Affinity |
| --- | --- |
| 1,25-dihydroxyvitamin $D_3$ (control) | 1 |
| Compound 1 | 11 |
| Compound 2 | 1/250 |
| Compound 3 | 1/50 |
| Compound 4 | 1/3 |

As shown in Table 2, it was found that Compound 1 had 11 times higher affinity for the $D_3$ receptor than $1\alpha,25$-dihydroxyvitamin $D_3$, the control.

Experimental Example 3
Assay of Affinity for Vitamin D-Binding Protein

The serum of vitamin D-deficient rat was diluted 1:10000 with 3.5 mM barbiturate buffer solution (pH 8.6) containing 0.13 M NaCl. Separately, to a culture tube, 40 μl each of the test compound ethanol solutions of varying concentrations (95% ethanol solutions; 1, 2, 4, 8, 16, 32, 63, 125, 250, 500, 1000 and 2000 ng/40p1) and tritium-labeled 25-hydroxyvitamin $D_3$ (4.44 TBq/mmol) 11000 dpm/30 μl (95% ethanol solution) were added in advance. Then, 500 μl of the diluted solution of vitamin D deficient rat serum was added to each culture tube, which was then subjected to vortex stirring. After incubation at 4° C. for 1 hour, 250 μL of DCC suspension was added and vortex-stirred. Each of the culture tubes was allowed to stand for 15 minutes at 4° C., and centrifuged at 3000 rpm at 4° C. for 10 minutes. With 500 μl of the supernatant, the radioactivity was determined. Then, the percentage of tritium-labeled 25-hydroxyvitamin $D_3$ bound to vitamin D-binding protein was obtained to determine the concentration of each test compound at which 50% of the tritium-labeled 25-hydroxyvitamin $D_3$ bound to the vitamin D-binding protein was replaced with the test compound ($ED_{50}$). As for Compounds 1, 2 and 3, 30% replacement values were determined because the affinity for the protein of these compounds was so low. As a control, the same procedures were followed using 1a,25-dihydroxyvitamin $D_3$, and $ED5_0$ of this control was obtained. Using the $ED_{50}$ of the control as the reference, i.e., 1, the biding affinity of each test compound was calculated as shown in Table 3.

TABLE 3

| Test Compounds | Affinity |
| --- | --- |
| 1,25-dihydroxyvitamin $D_3$ (control) | 1 |
| Compound 1 | 1/500 |
| Compound 2 | 1/500 |
| Compound 3 | 1/220 |
| Compound 4 | 2/3 |

As shown in Table 3, it was found that Compound 1 had the lowest affinity for the vitamin D-binding protein among the four compounds.

From the findings obtained in the above Experimental Examples, it was found that (20S,22R)-22-methyl-$1\alpha,25$-dihydroxyvitamin $D_3$ obtained in Example 1 has a high affinity for the $1\alpha,25$-dihydroxyvitamin $D_3$ receptor, whereas its affinity for vitamin D-binding protein was low.

Example of Pharmaceutical Preparation (Soft capsule)

In 600 g of O.D.O. (triglycerides of fatty acids of middle length; Nissin Oil Mills Ltd.), 1 mg of (20S,22R)-22-methyl-$1\alpha,25$-dihydroxyvitamin $D_3$ was dissolved, to which 30 mg of sorbic acid was added as a stabilizing agent. With the resulting mixture, soft capsules were prepared by an apparatus for producing gelatin-coated soft capsules according to a conventional method, each capsule containing 0.1 μg of (20S,22R)-22-methyl-$1\alpha,25$-dihydroxyvitamin $D_3$.

The present invention being thus described, it will be obvious that the same may be varied in many ways. Such variations are not to be regarded as a departure from the spirit and scope of the invention, and all such modifications as would be obvious to one skilled n the art are intended to be included within the scope of the following claims.

What is claimed is:

1. A composition for improving calcium metabolism comprising, as an active ingredient, (20S,22R)-22-methyl-1α,25-dihydroxyvitamin $D_3$ represented by the following formula (I):

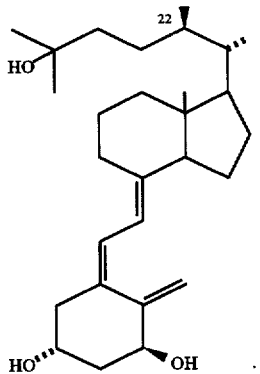

2. A method of treating a calcium metabolism disorder in a mammal, comprising administering to the mammal a therapeutically effective amount of (20S,22R)-22-methyl-1α,25-dihydroxyvitamin $D_3$ represented by the following formula (I):

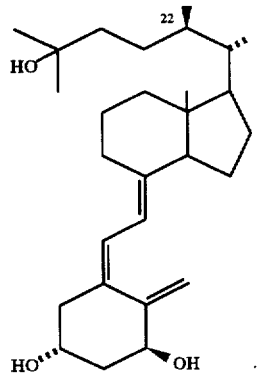

3. The method according to claim wherein the calcium metabolism disorder is hyperparathyroidism.

* * * * *